(12) United States Patent
Doi et al.

(10) Patent No.: US 8,238,624 B2
(45) Date of Patent: Aug. 7, 2012

(54) HYBRID MEDICAL IMAGE PROCESSING

(75) Inventors: Munehiro Doi, Yasu (JP); Moon J. Kim, Wappingers Falls, NY (US); Yumi Mori, Yamato (JP); James R. Moulic, Poughkeepsie, NY (US); Hiroki Nakano, Shiga (JP); Hiroki Nishiyama, Yamato (JP)

(73) Assignee: International Business Machines Corporation, Armonk, NY (US)

( * ) Notice: Subject to any disclaimer, the term of this patent is extended or adjusted under 35 U.S.C. 154(b) by 903 days.

(21) Appl. No.: 11/782,170

(22) Filed: Jul. 24, 2007

(65) Prior Publication Data

US 2008/0181472 A1    Jul. 31, 2008

Related U.S. Application Data

(63) Continuation-in-part of application No. 11/668,875, filed on Jan. 30, 2007, now Pat. No. 7,876,940.

(51) Int. Cl.
    *G06K 9/00*    (2006.01)
(52) U.S. Cl. .......................... 382/128; 382/100; 345/502
(58) Field of Classification Search .................. 382/128, 382/131, 302, 129, 130; 345/505; 600/407
    See application file for complete search history.

(56) References Cited

U.S. PATENT DOCUMENTS

| | | | |
|---|---|---|---|
| 4,517,593 A | | 5/1985 | Keller et al. |
| 4,893,188 A | | 1/1990 | Murakami et al. |
| 5,136,662 A | | 8/1992 | Maruyama et al. |
| 5,506,999 A | | 4/1996 | Skillman et al. |
| 5,621,811 A | * | 4/1997 | Roder et al. .................. 382/147 |
| 5,659,630 A | * | 8/1997 | Forslund ........................ 382/149 |
| 5,721,883 A | | 2/1998 | Katsuo et al. |
| 5,809,078 A | | 9/1998 | Tani et al. |
| 5,956,081 A | | 9/1999 | Katz et al. |
| 6,023,637 A | * | 2/2000 | Liu et al. ........................ 600/474 |
| 6,025,854 A | | 2/2000 | Hinz et al. |
| 6,081,659 A | * | 6/2000 | Garza et al. ...................... 716/52 |

(Continued)

FOREIGN PATENT DOCUMENTS

EP    1345120 A2    9/2003

(Continued)

OTHER PUBLICATIONS

Kuhnen, Leila, "Invitation to Pay Additional Fees—Communication Relating to the Results of the Partial International Search", PCT International Searching Authority, Apr. 25, 2008.

(Continued)

*Primary Examiner* — Vikkram Bali
*Assistant Examiner* — Nancy Bitar
(74) *Attorney, Agent, or Firm* — Hoffman Warnick LLC; William E. Schiesser

(57) ABSTRACT

The present invention uses a common, hybrid system platform to provide a generalized medical image processing system that can handle the existing medical image application as it is and route the compute intensive medical image processing to a multi-core processor/processing system. The invention allows the processing platform to be shared among healthcare system such as mammography, X-ray, CT Scan MRI, two-photon, laser microscopy, digital pathology, etc. It also allows the processing platform to deliver medical images to a variety of client devices, such as a desktop computer or a handheld device, through the network without high-performance graphical display capabilities because the rendering of the medical images is performed on the Cell BE based platform of the invention.

16 Claims, 15 Drawing Sheets

U.S. PATENT DOCUMENTS

| | | | |
|---|---|---|---|
| 6,166,373 A | 12/2000 | Mao | |
| 6,215,898 B1 | 4/2001 | Woodfill et al. | |
| 6,404,902 B1 | 6/2002 | Takano et al. | |
| 6,456,737 B1 | 9/2002 | Woodfill et al. | |
| 6,487,619 B1 | 11/2002 | Takagi | |
| 6,549,992 B1 | 4/2003 | Armangau et al. | |
| 6,567,622 B2 | 5/2003 | Phillips | |
| 6,647,415 B1 | 11/2003 | Olarig et al. | |
| 6,661,931 B1 | 12/2003 | Kawada | |
| 6,671,397 B1 | 12/2003 | Mahon et al. | |
| 6,744,931 B2 | 6/2004 | Komiya et al. | |
| 6,825,943 B1 * | 11/2004 | Barry et al. | 358/1.15 |
| 6,829,378 B2 | 12/2004 | DiFilippo et al. | |
| 6,898,634 B2 | 5/2005 | Collins et al. | |
| 6,898,670 B2 | 5/2005 | Nahum | |
| 6,950,394 B1 | 9/2005 | Chou et al. | |
| 7,000,145 B2 | 2/2006 | Werner et al. | |
| 7,016,996 B1 | 3/2006 | Schober | |
| 7,043,745 B2 | 5/2006 | Nygren et al. | |
| 7,065,618 B1 | 6/2006 | Ghemawat et al. | |
| 7,076,569 B1 | 7/2006 | Bailey et al. | |
| 7,095,882 B2 | 8/2006 | Akahori | |
| 7,102,777 B2 | 9/2006 | Haraguchi | |
| 7,106,895 B1 * | 9/2006 | Goldberg et al. | 382/144 |
| 7,142,725 B2 * | 11/2006 | Komiya et al. | 382/284 |
| 7,171,036 B1 | 1/2007 | Liu et al. | |
| 7,225,324 B2 | 5/2007 | Huppenthal et al. | |
| 7,243,116 B2 | 7/2007 | Suzuki et al. | |
| 7,299,322 B2 | 11/2007 | Hosouchi et al. | |
| 7,327,889 B1 | 2/2008 | Imai et al. | |
| 7,430,622 B1 | 9/2008 | Owen | |
| 7,480,441 B2 | 1/2009 | Klausberger et al. | |
| 7,523,148 B2 | 4/2009 | Suzuki et al. | |
| 7,602,394 B2 | 10/2009 | Seki et al. | |
| 7,605,818 B2 | 10/2009 | Nagao et al. | |
| 7,743,087 B1 | 6/2010 | Anderson et al. | |
| 7,801,895 B2 | 9/2010 | Hepper et al. | |
| 8,052,272 B2 | 11/2011 | Smith et al. | |
| 8,078,837 B2 | 12/2011 | Kajihara | |
| 8,094,157 B1 | 1/2012 | Le Grand | |
| 2002/0002636 A1 | 1/2002 | Vange et al. | |
| 2002/0129216 A1 | 9/2002 | Collins | |
| 2002/0164059 A1 * | 11/2002 | DiFilippo et al. | 382/128 |
| 2002/0198371 A1 | 12/2002 | Wang | |
| 2003/0031355 A1 | 2/2003 | Nagatsuka | |
| 2003/0053118 A1 * | 3/2003 | Muramoto et al. | 358/1.15 |
| 2003/0092980 A1 | 5/2003 | Nitz | |
| 2003/0113034 A1 | 6/2003 | Komiya et al. | |
| 2004/0024810 A1 | 2/2004 | Choubey et al. | |
| 2004/0062265 A1 | 4/2004 | Poledna | |
| 2004/0062454 A1 | 4/2004 | Komiya et al. | |
| 2004/0091243 A1 | 5/2004 | Theriault et al. | |
| 2004/0122790 A1 * | 6/2004 | Walker et al. | 707/1 |
| 2004/0143631 A1 | 7/2004 | Banerjee et al. | |
| 2004/0153751 A1 | 8/2004 | Marshal et al. | |
| 2004/0156546 A1 * | 8/2004 | Kloth | 382/181 |
| 2004/0170313 A1 | 9/2004 | Nakano et al. | |
| 2004/0186371 A1 | 9/2004 | Toda | |
| 2004/0217956 A1 | 11/2004 | Besl et al. | |
| 2004/0228515 A1 | 11/2004 | Okabe et al. | |
| 2004/0233036 A1 * | 11/2004 | Sefton | 340/5.53 |
| 2004/0252467 A1 | 12/2004 | Dobbs et al. | |
| 2005/0013960 A1 | 1/2005 | Ozeki et al. | |
| 2005/0022038 A1 | 1/2005 | Kaushik et al. | |
| 2005/0044132 A1 | 2/2005 | Campbell et al. | |
| 2005/0063575 A1 | 3/2005 | Ma et al. | |
| 2005/0080928 A1 | 4/2005 | Beverly et al. | |
| 2005/0083338 A1 | 4/2005 | Yun et al. | |
| 2005/0084137 A1 | 4/2005 | Kim et al. | |
| 2005/0093990 A1 | 5/2005 | Aoyama | |
| 2005/0113960 A1 | 5/2005 | Karau et al. | |
| 2005/0126505 A1 | 6/2005 | Gallager et al. | |
| 2005/0219253 A1 | 10/2005 | Piazza et al. | |
| 2005/0259866 A1 | 11/2005 | Jacobs et al. | |
| 2005/0263678 A1 | 12/2005 | Arakawa | |
| 2006/0013473 A1 | 1/2006 | Woodfill et al. | |
| 2006/0117238 A1 | 6/2006 | DeVries et al. | |
| 2006/0135117 A1 | 6/2006 | Laumen et al. | |
| 2006/0149798 A1 | 7/2006 | Yamagami | |
| 2006/0171452 A1 | 8/2006 | Waehner | |
| 2006/0184296 A1 | 8/2006 | Voeller et al. | |
| 2006/0190627 A1 * | 8/2006 | Wu et al. | 709/249 |
| 2006/0235863 A1 | 10/2006 | Khan | |
| 2006/0239194 A1 | 10/2006 | Chapell | |
| 2006/0250514 A1 | 11/2006 | Inoue et al. | |
| 2006/0268357 A1 | 11/2006 | Vook et al. | |
| 2006/0269119 A1 * | 11/2006 | Goldberg et al. | 382/144 |
| 2006/0274971 A1 | 12/2006 | Kumazawa et al. | |
| 2006/0279750 A1 | 12/2006 | Ha | |
| 2007/0126744 A1 | 6/2007 | Tsutsumi | |
| 2007/0159642 A1 | 7/2007 | Choi | |
| 2007/0245097 A1 | 10/2007 | Gschwind et al. | |
| 2007/0250519 A1 | 10/2007 | Fineberg et al. | |
| 2008/0013862 A1 | 1/2008 | Isaka et al. | |
| 2008/0036780 A1 | 2/2008 | Liang et al. | |
| 2008/0063387 A1 | 3/2008 | Yahata et al. | |
| 2008/0092744 A1 | 4/2008 | Storbo et al. | |
| 2008/0129740 A1 | 6/2008 | Itagaki et al. | |
| 2008/0140771 A1 | 6/2008 | Vass et al. | |
| 2008/0144880 A1 | 6/2008 | DeLuca | |
| 2008/0147781 A1 | 6/2008 | Hopmann et al. | |
| 2008/0177964 A1 | 7/2008 | Takahashi et al. | |
| 2008/0259086 A1 | 10/2008 | Doi et al. | |
| 2008/0260297 A1 | 10/2008 | Chung et al. | |
| 2008/0263154 A1 | 10/2008 | Van Datta | |
| 2008/0270979 A1 | 10/2008 | McCool et al. | |
| 2009/0003542 A1 | 1/2009 | Ramanathan et al. | |
| 2009/0052542 A1 | 2/2009 | Romanovskiy et al. | |
| 2009/0066706 A1 | 3/2009 | Yasue et al. | |
| 2009/0074052 A1 | 3/2009 | Fukuhara et al. | |
| 2009/0083263 A1 | 3/2009 | Felch et al. | |
| 2009/0089462 A1 | 4/2009 | Strutt | |
| 2009/0150555 A1 | 6/2009 | Kim et al. | |
| 2009/0150556 A1 | 6/2009 | Kim et al. | |
| 2009/0187654 A1 | 7/2009 | Raja et al. | |
| 2009/0265396 A1 | 10/2009 | Ram et al. | |
| 2010/0060651 A1 | 3/2010 | Gala et al. | |

FOREIGN PATENT DOCUMENTS

| | | |
|---|---|---|
| WO | 0068884 A1 | 11/2000 |
| WO | 2008092744 A2 | 8/2008 |

OTHER PUBLICATIONS

Anh Hong Do, Notice of Allowance and Fee(s) Due dated Aug. 13, 2010 for U.S. Appl. No. 11/668,875, 9 pages.

Patent Cooperation Treaty, PCT/EP2008/050443, PCT International Preliminary Report on Patentability and Written Opinion of the International Searching Authority dated Aug. 4, 2009, 8 pages.

Patent Cooperation Treaty, PCT/EP2008/050443, PCT International Search Report dated Jul. 22, 2008, 7 pages.

Do, U.S. Appl. No. 11/668,875, Notice of Allowance & Fees Due, Aug. 13, 2010, 9 pages.

Tsai, U.S. Appl. No. 11/738,723, Office Action Communication, Jun. 24, 2010, 26 pages.

Yang, U.S. Appl. No. 11/767,728, Office Action Communication, Nov. 19, 2010, 25 pages.

Chambers, U.S. Appl. No. 11/951,709, Office Action Communication, Nov. 17, 2009, 20 pages.

Tsai, U.S. Appl. No. 11/738,711, Office Action Communication, Jun. 25, 2010, 26 pages.

Tsai, U.S. Appl. No. 11/738,711, Office Action Communication, Nov. 9, 2010, 13 pages.

Ansari, U.S. Appl. No. 11/940,506, Office Action Communication, Oct. 29, 2010, 21 pages.

Ansari, U.S. Appl. No. 11/940,506, Office Action Communication, May 14, 2010, 16 pages.

Ansari, U.S. Appl. No. 11/940,506, Office Action Communication, Nov. 2, 2009, 20 pages.

Cosby, U.S. Appl. No. 11/940,470, Office Action Communication, Nov. 26, 2010 19 pages.

Cosby, U.S. Appl. No. 11/940,470, Office Action Communication, Jun. 9, 2010, 26 pages.

Cosby, U.S. Appl. No. 11/940,470, Office Action Communication, Nov. 18, 2009, 31 pages.

Yang, U.S. Appl. No. 11/877,926, Office Action Communication, Nov. 22, 2009, 33 pages.
Chambers, U.S. Appl. No. 11/951,709, Office Action Communication, Nov. 29, 2010, 21 pages.
Chambers, U.S. Appl. No. 11/951,709, Office Action Communication, May 14, 2010, 24 pages.
Sole, PCT / EP2008 / 054331, International Search Report and the Written Opinion of the International Searching Authority, Oct. 4, 2008, 10 pages.
Tiv, U.S. Appl. No. 11/951,712, Office Action Communication, Jan. 5, 2011, 18 pages.
Tiv, U.S. Appl. No. 11/951,712, Office Action Communication, Jul. 23, 2010, 25 pages.
Tran, U.S. Appl. No. 11/951,712, Office Action Communication, Sep. 9, 2009, 26 pages.
Do, U.S. Appl. No. 11/668,875, Notice of Allowance & Fees Due, Sep. 20, 2010, 8 pages.
Tsung Yin Tsai, U.S. Appl. No. 11/738,711, Office Action Communication, Feb. 18, 2011, 17 pages.
Tsung Yin Tsai, U.S. Appl. No. 11/738,723, Office Action Communication, Feb. 18, 2011, 17 pages.
Cosby, Lawrence V., U.S. Appl. No. 11/940,470, Office Action Communication, Mar. 4, 2011, 22 pages.
Yang, Qian, U.S. Appl. No. 11/877,926, Office Action Communication, Mar. 23, 2011, 32 pages.
Yang, Qian, U.S. Appl. No. 11/767,728, Office Action Communication, Mar. 15, 2011, 34 pages.
Tsung Yin Tsai, Office Action Communication for U.S. Appl. No. 11/738,723 dated May 23, 2011, 16 pages.
Tsung Yin Tsai, Office Action Communication for U.S. Appl. No. 11/738,711 dated May 23, 2011, 16 pages.
Tiv, Backhean, Office Action Communication for U.S. Appl. No. 11/951,712 dated Apr. 26, 2011, 20 pages.
Yang, U.S. Appl. No. 11/767,728, Office Action Communication, Jul. 28, 2011, 32 pages.
Chambers, U.S. Appl. No. 11/951,709, Office Action Communication, Dec. 20, 2011, 40 pages.
Cosby, U.S. Appl. No. 11/940,470, Office Action Communication, Dec. 22, 2011, 41 pages.
Yang, U.S. Appl. No. 11/877,926, Office Action Communication, Jan. 4, 2012, 40 pages.
Tsai, U.S. Appl. No. 11/738,723, Office Action Communication, Sep. 27, 2011, 20 pages.
Tsai, U.S. Appl. No. 11/738,711, Office Action Communication, Sep. 23, 2011, 20 pages.
Tiv, U.S. Appl. No. 11/951,712, Office Action Communication, Oct. 21, 2011, 27 pages.
Yang, U.S. Appl. No. 11/767,728, Office Action Communication, Oct. 28, 2011, 33 pages.
Tsai, U.S. Appl. No. 11/738,723, Office Action Communication, Nov. 4, 2011, 15 pages.
Entezari, U.S. Appl. No. 12/028,073, Office Action Communication, Dec. 2, 2011, 51 pages.
Tsai, U.S. Appl. No. 11/738,711, Office Action Communication, Nov. 4, 2011, 14 pages.
Chambers, U.S. Appl. No. 11/951,709, Office Action Communication, Mar. 21, 2012, 27 pages.
Entezari, U.S. Appl. No. 12/028,073, Notice of Allowance & Fees Due, Mar. 21, 2012, 18 pages.
Yang, U.S. Appl. No. 11/767,728, Office Action Communication, Feb. 16, 2012, 33 pages.
Yang, U.S. Appl. No. 11/877,926, Office Action Communication, Apr. 27, 2012, 32 pages.
Yang, U.S. Appl. No. 11/767,728, Office Action Communication, May 21, 2012, 49 pages.
Tsai, U.S. Appl. No. 11/738,711, Notice of Allowance & Fees Due, May 25, 2012, 5 pages.
Tsai, U.S. Appl. No. 11/738,723, Notice of Allowance & Fees Due, May 25, 2012, 31 pages.
Kim, U.S. Appl. No. 12/057,942, Office Action Communication, Jun. 7, 2012, 58 pages.

* cited by examiner

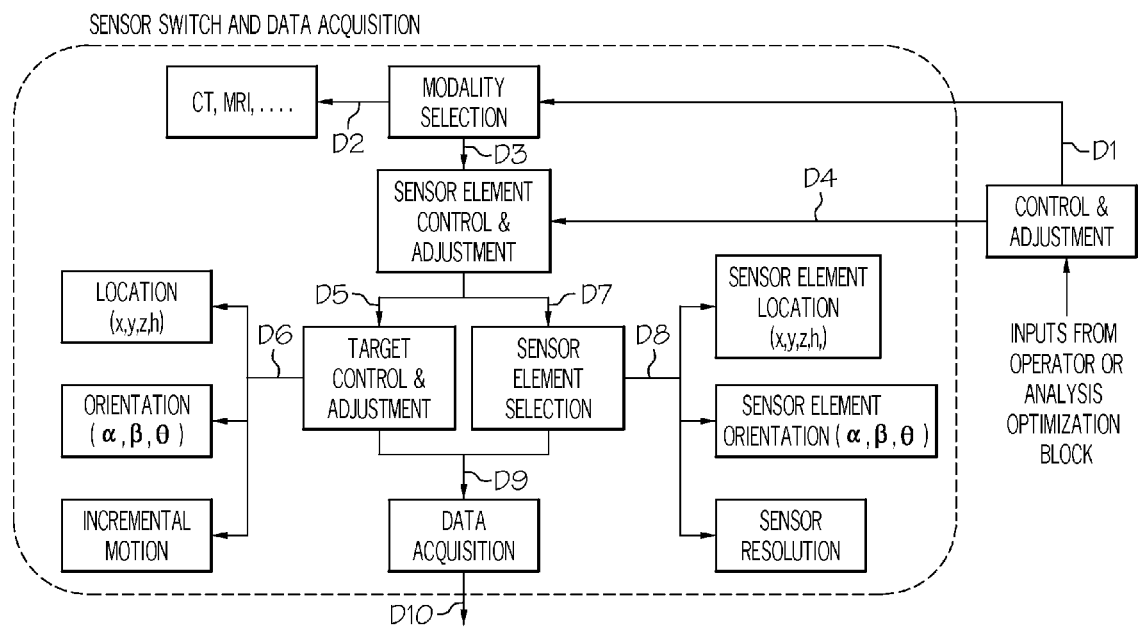

1. MODALITY SELECTION SETTINGS LOADED FROM OPERATOR OR PROFILE
2. SPECIFIC TEST MODALITY CHOSEN
3. CORRESPONDING SENSOR ELEMENTS ACTIVATED TO SUPPORT SELECTED MODALITY
4. SENSOR ELEMENT SETTINGS PROFILE OR DYNAMIC RECONFIGURATION SETTINGS FROM ANALYSIS AND OPTIMIZATION BLOCK
5. & 6. TARGET POSITIONING ( LOCATION, ORIENTATION AND INCREMENTAL MOTION) LOADED
7. & 8. SENSOR ELEMENT POSITIONING ( LOCATION, ORIENTATION AND RESOLUTION) LOADED
9. DATA ACQUISITION INITIATED
10. COLLECTED DATA SENT ON TO FILTERING, PRE-PROCESSING
REPEATING STEPS 4 - 10 WILL OCCUR OF REAL-TIME RECONFIGURATION OF TARGET AND SENSOR ELEMENT SETTINGS

FIG. 3

HYBRID MEDICAL IMAGE PROCESSING

CROSS-REFERENCE TO RELATED APPLICATION

This application is a continuation-in-part (CIP) application of commonly owned and patent application Ser. No. 11/668,875, entitled "UNIVERSAL IMAGE PROCESSING", filed Jan. 30, 2007, now U.S. Pat No. 7,876,940 the entire contents of which are herein incorporated by reference. This application is also related in some aspects to commonly owned and co-pending application Ser. No. 11/767,728, entitled "HYBRID IMAGE PROCESSING SYSTEM", filed Jun. 25, 2007, the entire contents of which are herein incorporated by reference. This application is also related in some aspects to commonly owned and co-pending application Ser. No. 11/738,723, entitled "HETEROGENEOUS IMAGE PROCESSING SYSTEM", filed Apr. 23, 2007, the entire contents of which are herein incorporated by reference. This application is also related in some aspects to commonly owned patent application Ser. No. 11/738,711, entitled "HETEROGENEOUS IMAGE PROCESSING SYSTEM", filed Apr. 23, 2007, the entire contents of which are herein incorporated by reference.

FIELD OF THE INVENTION

This invention generally relates to medical image processing. Specifically, the present invention provides a hybrid processing method, system, and program product that can be implemented across different platforms.

BACKGROUND OF THE INVENTION

Modern day medical and biomolecular imaging scanners can generate large amounts of data in a short period of time, usually requiring a dedicated computer for processing and visualization. For indirect medical imaging modalities/devices, such as MRI, PET and CT, the raw data, commonly called k-space data, needs to be mathematically transformed into medical images which require super scale computing power. This process, called medical image reconstruction, can take hours using current systems and severely limits clinical use of medial imaging applications.

Recent advances in multi-core computer processor technology will drastically reduce medical image processing time. It will also open the door to new possibilities of sharing computer intensive processors among the modalities. Emerging multi-core processors are able to accelerate medical imaging applications by exploiting the parallelism available in their algorithms. Unfortunately all existing systems require a separate processing system for each imaging device, which is both costly and decentralized. Moreover, modern day medical and biomolecular imaging scanners can generate huge amounts of data in a short period of time, usually requiring a dedicated computer for processing and visualization. In view of the foregoing, there exists a need for

SUMMARY OF THE INVENTION

In general, the present invention uses a common, hybrid system platform to provide a generalized medical image processing system that can handle the existing medical image application as it is and route the computer intensive medical image processing to a multi-core processor/processing system. The invention allows the processing platform to be shared among healthcare systems such as mammography, X-ray, CT Scan MRI, two-photon, laser microscopy, digital pathology, etc. It also allows the processing platform to deliver medical images to a variety of client devices, such as a desktop computer or a handheld device, through the network without high-performance graphical display capabilities because the rendering of the medical images is performed on the Cell BE based platform of the invention.

As such, this disclosure provides a hybrid medical image processing system. The invention allows a medical image processing system to be shared, controlled, adjusted by the user and is to process medical images by one type of platform and application and controls another platform. The invention permits sharing both computation and visualization across a hybrid platform, thus allowing for sharing of computing resources and visualization of medical images on a variety of imaging (client) devices without high-performance graphical display cards. In a typical embodiment a (e.g., medical) medical image 3D linear registration algorithm is implemented on a Cell Broadband Engine processor, which has multiple (e.g., nine) processor cores on a chip and has a 4-way SIMD unit for each core and other application, storage and control medical images on platforms other then Cell BE. One example that is described here is an Intel x86 platform (Intel is a trademark of Intel Corp. in the United States and/or other countries). However, the platform can be any other platform including mainframe.

A first aspect of the present invention provides a hybrid medical image processing system, comprising: a pre-processor for receiving raw medical image data from a set of modalities and for storing the raw medical image data in temporary storage; a medical image processor for processing the raw medical image data for viewing by medical professionals; and a post-processor for storing and retrieving processed medical image data, and for performing analytics on the processed medical image data.

A second aspect of the present invention provides a hybrid medical image processing system, comprising: a set of servers for receiving and storing medical image data in a server database, the set of servers comprising a server application, a medical image query application, and a medical image transfer application; and a set of processing systems for processing the medical image data, the set of processing systems comprising a cell application, a command dispatcher, a processing engine library, and a medical image transfer library.

A third aspect of the present invention provides a hybrid medical image processing method, comprising: receiving commands from a set of functional units on a set of processing systems; sending at least a subset of the commands to a set of servers; receiving medical image data from the set of servers; assigning tasks for processing the medical image data to a set of processing engines; processing the medical image data with the set of processing engines; and sending results of the processing to the set of functional units.

A fourth aspect of the present invention provides a program product stored on at least one computer readable medium for processing medical images, the at least one computer readable medium comprising program code for causing at least one computer system to: receive commands from a set of functional units on a set of processing systems; send at least a subset of the commands to a set of servers; receive medical image data from the set of servers; assign tasks for processing the medical image data to a set of processing engines; process the medical image data with the set of processing engines; and send results of the processing to the set of functional units.

A fifth aspect of the present invention provides a method for deploying a hybrid medical image processing system, comprising: deploying a computer infrastructure being operable to: receive commands from a set of functional units on a set of processing systems; send at least a subset of the commands to a set of servers; receive medical image data from the set of servers; assign tasks for processing the medical image data to a set of processing engines; process the medical image data with the set of processing engines; and send results of the processing to the set of functional units.

A sixth aspect of the present invention provides computer software embodied in a propagated signal for processing medical images, the at least one computer software comprising instructions for causing at least one computer system to: receive commands from a set of functional units on a set of processing systems; send at least a subset of the commands to a set of servers; receive medical image data from the set of servers; assign tasks for processing the medical image data to a set of processing engines; process the medical image data with the set of processing engines; and send results of the processing to the set of functional units.

A seventh aspect of the present invention provides a computer-implemented hybrid medical image processing business method, comprising: receiving commands from a set of functional units on a set of processing systems; sending at least a subset of the commands to a set of servers; receiving medical image data from the set of servers; assigning tasks for processing the medical image data to a set of processing engines; processing the medical image data with the set of processing engines; and sending results of the processing to the set of functional units.

An eighth aspect of the present invention provides a data processing system for processing medical images, comprising: a memory medium comprising instructions; a bus coupled to the memory medium; and a processor coupled to the bus that when executing the instructions causes the data processing system to: receive commands from a set of functional units on a set of processing systems; send at least a subset of the commands to a set of servers; receive medical image data from the set of servers; assign tasks for processing the medical image data to a set of processing engines; process the medical image data with the set of processing engines; and send results of the processing to the set of functional units.

BRIEF DESCRIPTION OF THE DRAWINGS

These and other features of this invention will be more readily understood from the following detailed description of the various aspects of the invention taken in conjunction with the accompanying drawings in which:

FIG. 3 shows an image data acquisition process flow according to the present invention.

Figure 1:
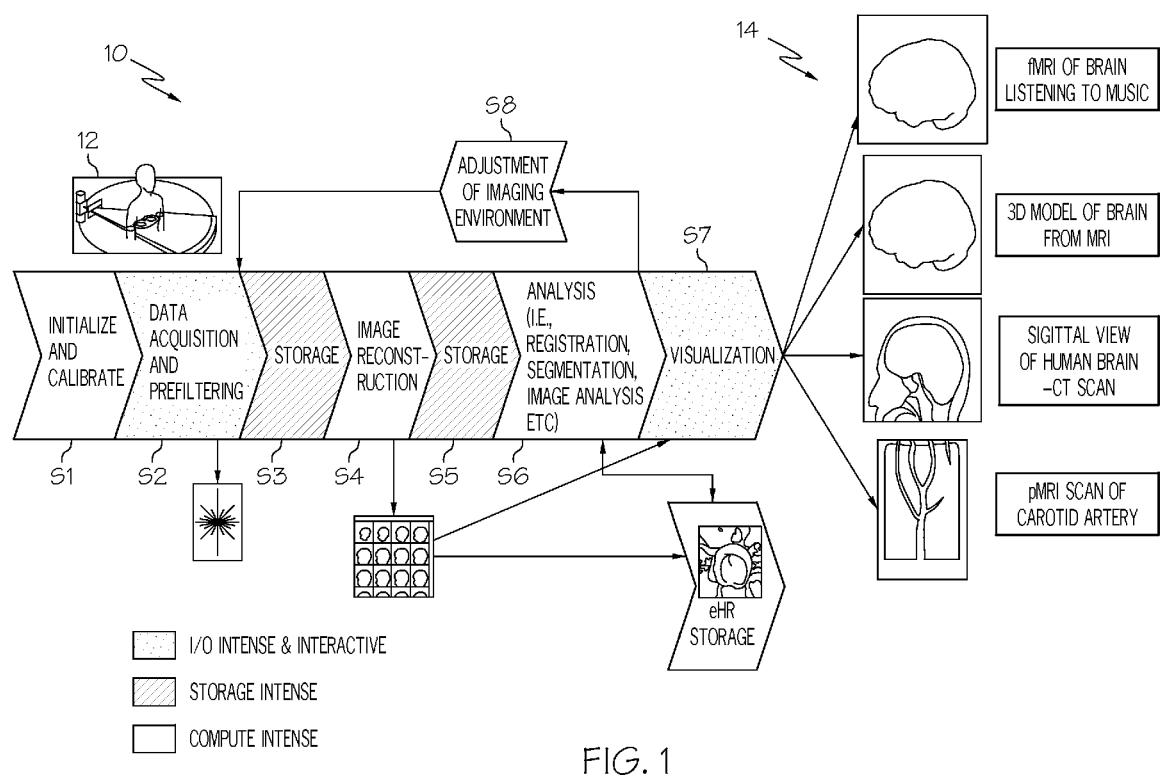
FIG. 1 shows a universal image processing workflow according to the present invention.

The drawings are not necessarily to scale. The drawings are merely schematic representations, not intended to portray specific parameters of the invention. The drawings are intended to depict only typical embodiments of the invention, and therefore should not be considered as limiting the scope of the invention. In the drawings, like numbering represents like elements.

DETAILED DESCRIPTION OF THE INVENTION

For convenience purposes, the Detailed Description of the Invention has the following sections:
 I. General Description
  A. Image Processing
  B. Processor Implementation
 II. Computerized Implementation I. General Description Medical Imaging is a broad, complex market providing an in-vivo and non-invasive lens through which to explore, evaluate, visualize, and interpret the information associated with the multifaceted structures and dynamic processes in healthy and sick tissues, and organs. It is maturing from the role of an important diagnostic support service to an even more significant fundamental and diverse role in global healthcare. Medical Imaging considers the patient in time, space, and context, from an anatomical view down to the molecular level, in tune with the developments of the "post-genomic era." These technologies when applied to areas ranging from cell and molecular biology to radiology, pathology, surgery, and physiology, will allow a more comprehensive understanding of and better care of the mind and body. New medical, molecular and radioisotope imaging methods reflect anatomy and dynamic body functions heretofore discerned only from hand-drawn textbook illustrations.

These new methods give functional medical images of blood flow, tumor identification, drug performance, and metabolism essential in the brain, heart, liver, stomach, kidneys, bone, and other organs. Many of today's medical imaging scanners are tomography-based; they take a number, anywhere between 16 and 1000, of two-dimensional medical images called "slices". Using a sophisticated computer algorithm the 2D slices, from the same modality (same patient at different times) or different modalities (i.e., PET and MRI), can be combined, or fused, into a single 3D medical image which can be rotated and translated to visualize the object that was scanned. The followings are some of medical image technologies:

(1) Emission-based tomography methods—PET, SPECT. These are an important part of molecular imaging—they are used mostly for brain, heart, and lung scans.

(2) Optical technologies—Fluorescence, digital microscopy, and Optical coherence tomography (OCT).

(3) Structural imaging methods—X-ray, CT, MRI, and Ultrasound—these are useful to provide an anatomical frame of reference onto which other molecular imaging scans can be transposed.

(4) Functional methods—fMRI is a technique for determining which parts of the brain are activated by different types of physical sensation or activity, such as sight, sound, or the movement of a subject's fingers.

Practically every medical imaging scanner purchased today comes with at least one dedicated computer system to manage the scanner and to analyze the raw medical image data. It is not uncommon for large hospitals, pharmaceutical companies and medical schools to have many imaging scanners in a single building. For example, a large hospital may have several MRI scanners with different strength magnets and bore sizes, PET, CT, Ultrasound, and X-ray systems. The computers associated with these scanners are dedicated and not shared between the different modalities even if one system is underutilized while a system down the hall cannot keep up with the computational demands being put on it.

Most new PET, CT and MRI scanners are configured with multiple collectors and the data is collected in parallel in 2D planes or 3D volumes. Modern parallel imaging methods have significantly reduced medical image acquisition time from about an hour down to several minutes or seconds. However, the large computational requirements associated with parallel imaging require new, efficient reconstruction processing. This implementation does not allow the computing resource to be shared with other applications and therefore the utilization of such a system is very low.

As indicated above, the present invention uses a common, hybrid system platform to provide a generalized medical image processing system that can handle the existing medical image application as it is and route the compute intensive medical image processing to a multi-core processor/processing system. The invention allows the processing platform to be shared among healthcare system such as mammography, X-ray, CT Scan MRI, two-photon, laser microscopy, digital pathology, etc. It also allows the processing platform to deliver medical images to a variety of client devices, such as a desktop computer or a handheld device, through the network without high-performance graphical display capabilities because the rendering of the medical images is performed on the Cell BE based platform of the invention.

As such, this disclosure provides a hybrid medical image processing system. The invention allows a medical image processing system to be shared, controlled, and adjusted by the user to process medical images by one type of platform and application and controlled by another platform. The invention permits sharing both computation and visualization across a hybrid platform, thus allowing for sharing of computing resources and visualization of medical images on a variety of imaging (client) devices without high-performance graphical display cards. In a typical embodiment a (e.g., medical) medical image 3D linear registration algorithm is implemented on a Cell Broadband Engine processor, which has multiple (e.g., nine) processor cores on a chip and has a 4-way SIMD unit for each core and other application, storage and control medical images on platforms other then Cell BE. One possible example that is described here is an Intel x86 platform (Intel is a trademark of Intel Corp. in the United States and/or other countries). However, the platform can be any other platform including mainframe. Accordingly, section IB below describes a particular processor implementation that enables the hybrid medical image processing of the present invention.

It should be understood in advance that although this disclosure describes the invention with respect to medial imaging, the teachings described herein could be applied to any other technology such as document scanning, photographs, etc.

A. Image Processing

FIGS. 1-6 are also described in parent patent application Ser. No. 11/668,875, which was cross-referenced and incorporated above. They will be depicted and described herein for convenience purposes. Referring now to FIG. 1, a medical image processing flow 10 according to the present invention is shown. As depicted, the imaging device 12 is initialized and calibrated in step S1. Along these lines, the present invention is especially advantageous because it is configured to communicate with multiple imaging devices. Specifically, the system of the present invention can communicate with any type (e.g., NMR, CT, desktop scanner, camera) of imaging device 12. Previous systems were local or specifically assigned to a particular imaging device. In any event, in step S2, medical image data is acquired from imaging device 12 and is prefiltered. At step S3, the medical image data can be temporarily stored for medical image reconstruction in step S4. The reconstructed medical image can then be stored in step S5 for analysis in step S6. Such analysis can include, among other things, registration and segmentation. After analysis, the medical image can be visualized in step S7 and a display 14 corresponding to imaging device 12. Thus, the present invention is also configured to communicate with any number of display devices.

Under the present invention feedback can also be generated and provided to imaging device 12. Specifically, as shown in step S8, the imaging environment can be adjusted based on the steps up through analysis S6. The feedback can also be used to enhance the data acquisition and prefiltering.

Figure 2:
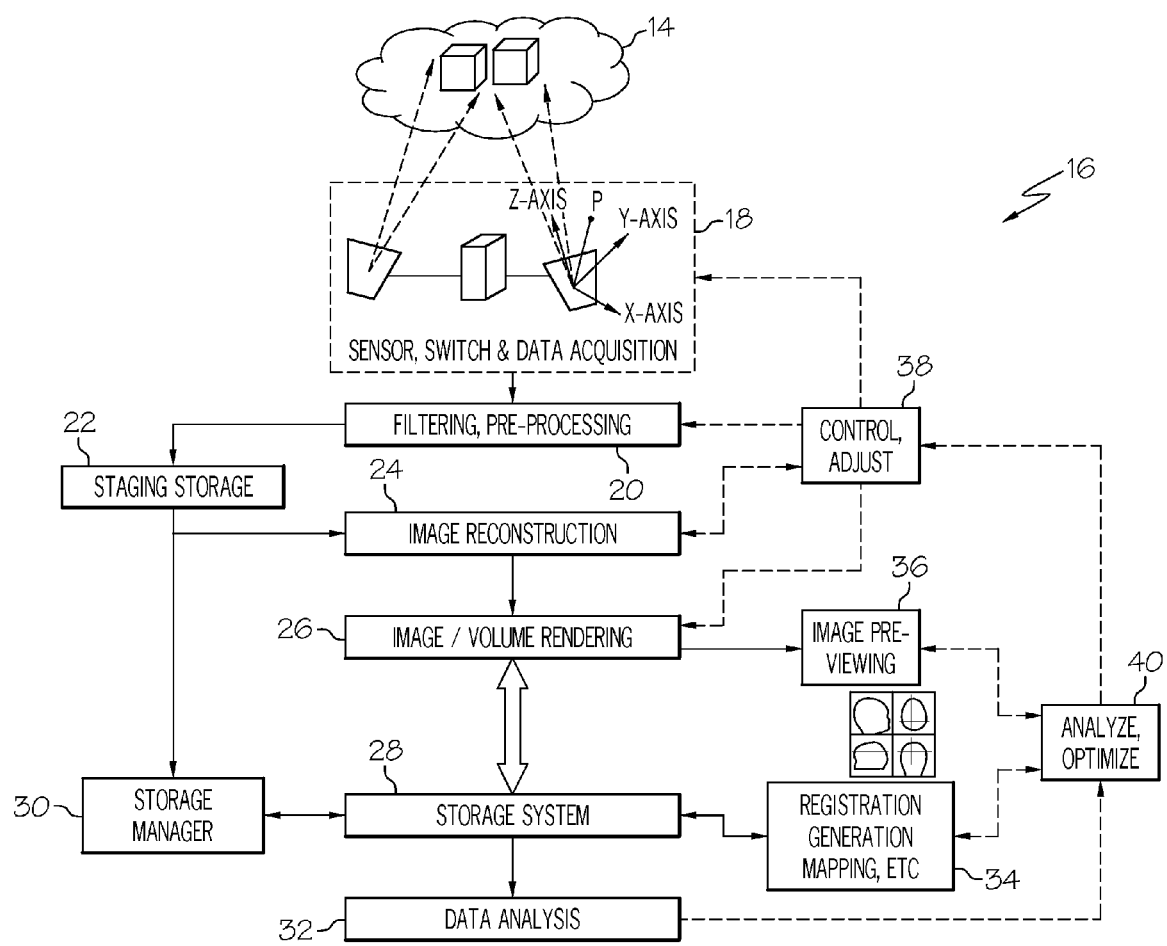
FIG. 2 shows a universal processing system according to the present invention.

Referring now to FIG. 2, these concepts are depicted in a system view 16 of the invention. In general, system 16 comprises the following modules:

Data acquisition module 18 having imaging device/modality 14 specific sensors, switch & data acquisition capabilities. As shown, system 16 is configured to communicate with multiple different types of imaging devices 14.

Filtering and preprocessing module 20 for prefiltering any artifacts or "noise" from the medical image data.

Staging storage 22 for providing temporary storage for the medical image data.

Medical image reconstruction module 24 for reconstructing a medical image from the medical image data stored in staging storage 22. Reconstruction algorithms are specific to each modality and there are many different algorithms for each. The algorithms typically employ some type of inverse transform such as Radon (PET) and FFT (MRI) or matrix inversion. The computational complexity of these algorithms can range from simple for 2D FFT to very complex for large matrix inversions. They can take anywhere from several minutes to tens of hours on a high-end desktop PC. Device/modality vendors usually include a medical image reconstruction application when the customer purchases their scanner.

Medical image/volume rendering module 26 for rendering the medical image on a display.

Medical image pre-viewing module 36 for providing a preview of the medical image if desired.

Storage system 28 and manager 30 for providing permanent storage for the medical image/medical image data.

Registration and mapping module 34 for registering and mapping the medical image.

Data processing and analysis module 32 for processing and analyzing the medical image/medical image data.

Analysis and optimization module 40 for optimizing the medical image/medical image data based on the analysis. This could include, among other things, eliminating additional artifacts. Analysis could include medical image registration (fusion), segmentation, and knowledge extraction (also know as feature detection, extraction and identification). Medical image analysis phases can be very computer intensive. The results of these phases are then stored along with the medical image in the central repository. Registration is the aligning or developing of correspondences between data from different modalities, such as PET and CT in order to combine the information contained in both or within the same modality as in MRI medical images for a single patient at different times. MRI scans for a patient are taken over a period of time, maybe once a month for 6 to 8 months. The medical images are fused together to give the doctor or research a view of the progress, or lack of progress, of the drug in question. Segmentation is the process of identifying and classifying data found in a digitally sampled representation. An example would be labeling and measuring the different features in a 3D MRI of a human brain. Visualization can be done after medical image reconstruction and medical image analysis. It is usually performed with a high-resolution graphics card in a desktop PC or workstation. Knowledge extraction involves searching and analysis of medical images in order to generate additional and/or new information that can be use by physicians, researchers, and other medical professionals. The new information may be combined with data from other sources such as genomics, proteomics and immunological data to help the physician make more informed and better decisions. The Cell BE multicore processing technology allows massive parallel medical image processing in a medical clinical application.

Feedback control and adjustment module 38 is for generating and providing the above-mentioned feedback to the respective imaging devices 14.

Although not shown, processing system 16 and/or imaging devices 14 can include a medical image transcoding, streaming, and display module. For example, once a medical image is ready to be viewed, it must be prepared for display on a client device. Some client devices, such as a desktop PC, have graphical display cards that are capable of rendering and displaying medical images. However, some devices, such as a web browser or handheld device, do not have the capability of rendering and displaying high-resolution medical images. Thus, it is necessary to render the medical images on the universal platform and then stream them to the client device. The streaming of a medical image must be transcoded, or tailored, to fit the display capabilities of each client device. In general, processing system 16 allows a medical image processing system to be shared, controlled, adjusted and optimized among all imaging devices/modalities and medical image analysis applications, and to deliver medical images to a variety of client devices.

The data collection phase is typically device/modality dependent and can take anywhere from minutes to hours. After the patient/specimen is scanned, the medical image can be generated using a modality dependent medical image reconstruction algorithm, and visualized. For each modality, there are a number of algorithms for medical image reconstruction. The algorithms typically employ an (inverse) FFT or matrix inversion phase and can be very computationally expensive. In some cases, this step can take several hours on a desktop PC.

Referring to FIG. 3, a data acquisition process flow according to the present invention is shown. In step D1, device/modality selection settings are loaded from an operator or profile. In step D2, a specific test device/modality is chosen. In step D3, corresponding sensor elements are activated to support the selected device/modality. In step D4, sensor element settings are determined for the analysis and optimization discussed above. In steps D5 and D6, target position (location, orientation, and incremental motion) settings are loaded. In step D7 and D8, sensor element positioning (location, orientation and resolution) settings are loaded. In step D9, data acquisition is initiated, and in Step D10, collected data is sent along to preprocessing and prefiltering. It should be noted that steps D4-D10 can be repeated in real-time.

Figure 4:
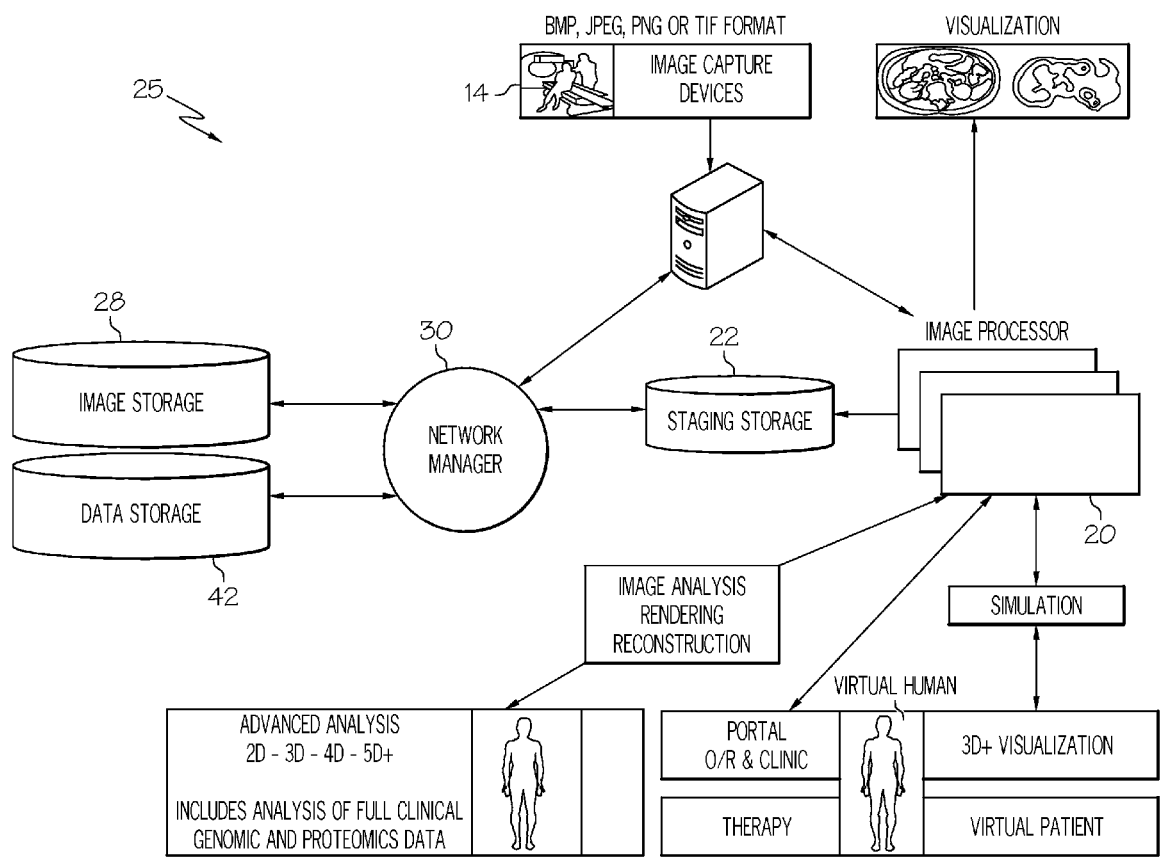
FIG. 4 shows an image data storage architecture according to the present invention.

Referring now to FIG. 4, a medical image data storage architecture 25 according to the present invention is shown. As described above, medical image data is acquired for an imaging device 14 and processed/pre-filtered by prefiltering module 20, after which the medical image data can be temporarily stored in staging storage system 22. After the medical image is reconstructed, it can be permanently stored by network manager 30 in medical image storage system 28. Similarly the corresponding medical image data can be stored in data storage system 42. Aside from the storage options shown in FIG. 4, the present invention will perform any addition operations described above such as medical image analysis, rendering and reconstruction, simulation, etc.

Figure 5:
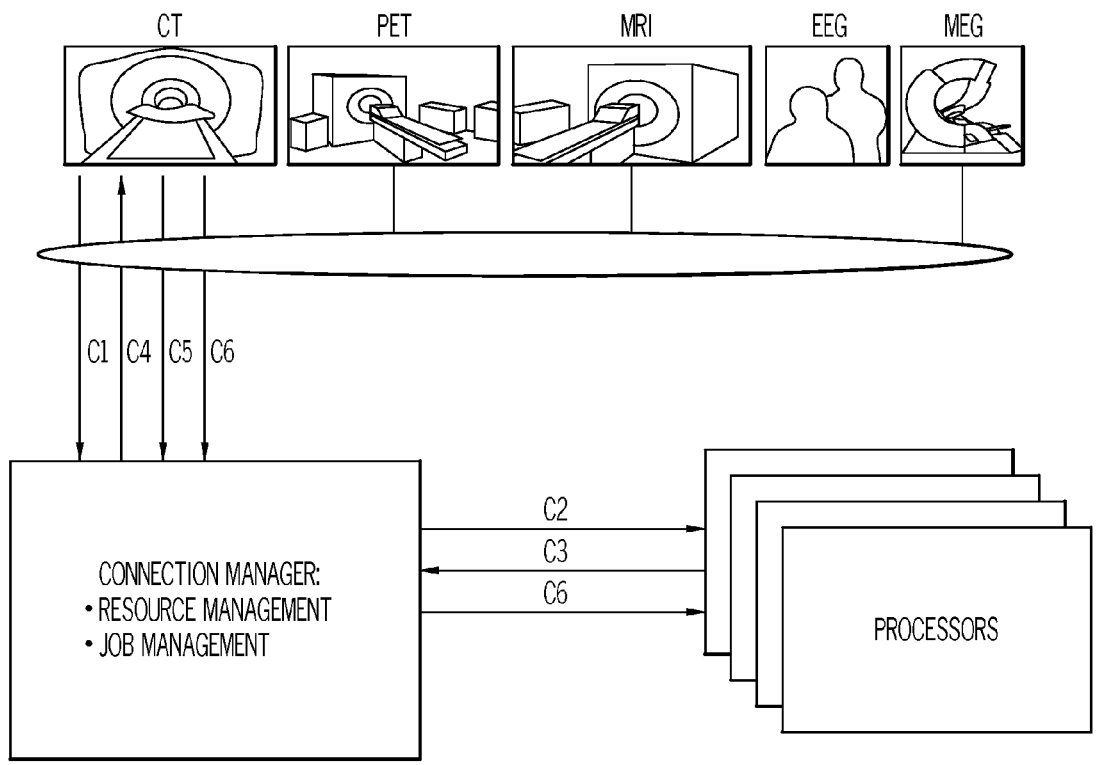
FIG. 5 shows a diagram of a connection protocol according to the present invention.

FIG. 5 shows a diagram of a connection protocol according to the present invention. When a device/modality initiates medical image scanning, it sends a signal to the connection manager by querying the resources and the connection sequence as follows. The scanning is done in parallel. The connection sequence is as follows: In step C1, the resource is queried. In step C2 the processors are queried. In step C3, the status of processors is determined based on the querying. In step C4, a particular device is selected. In step C5, a processor is selected. In step C6 scanning data is sent to the selected processor for processing.

Figure 6:
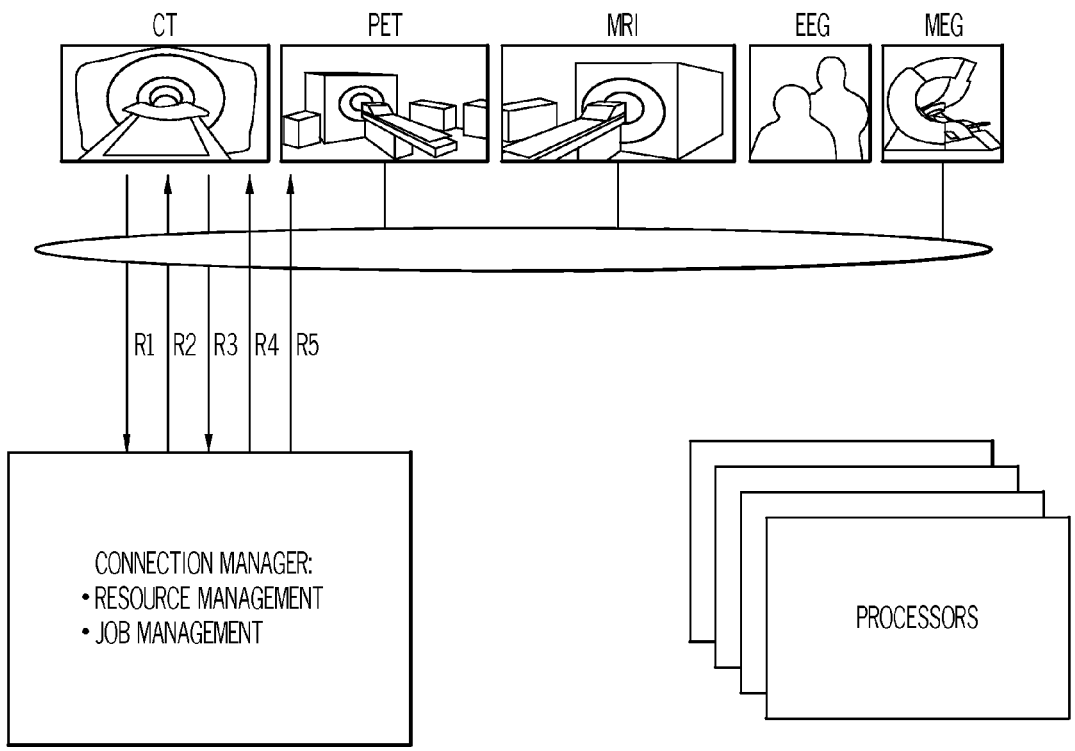
FIG. 6 shows a diagram of a resource set up protocol according to the present invention.

FIG. 6 shows a diagram of a resource set up protocol for a new imaging device or device type according to the present invention. Specifically, when a new device/modality is brought in to the system, the set up sequence is as follows: In step R1, the resource is registered. In step R2, a machine attribute is requested. In step R3, the attributes are sent from the imaging device. In step R4 a connection package is sent back to the imaging device. In step R5, a connection file is then downloaded to the imaging device.

B. Processor Implementation

Figure 7:
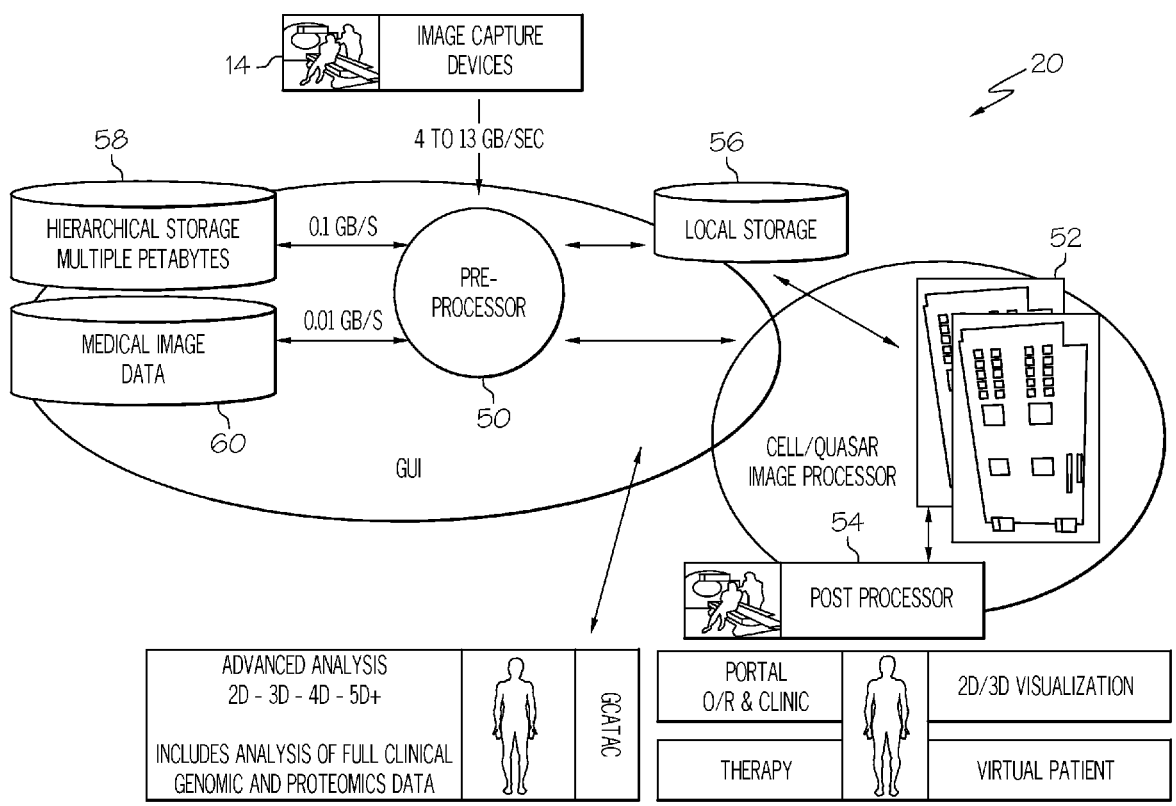
FIG. 7 shows a processing system view according to the present invention.

Reference will now be made to FIGS. 7-14, which describe a specific processor/processing system implementation and accompanying software stack implementation that enable the hybrid medical image processing functions of the present invention. Referring first to FIG. 7, an ecosystem view of processor system 20 is shown. In general, this implementation includes a set (e.g., at least one) of processors for providing multi stage processing of medical image data. In a typical embodiment, the set of processors are QSXX (e.g., QS21) processors. Along these lines, processing system include: a pre-processor 50 for receiving raw medical image data from a set of modalities/image capture devices 14 and for storing the raw medical image data in temporary storage; a medical image processor 52 for processing the raw medical image data (e.g., for registration, segmentation, fusion, etc.) for viewing by medical professionals; and a post-processor 54 for storing and retrieving processed medical image data, and for performing analytics (e.g., searching for a particular pattern) on the processed medical image data. Along these lines, this implementation can leverage one or more storage devices such as local storage 56, hierarchical storage 58, and/or medical image data storage 60. In addition, the set of modalities 14 can be any type of medical image capturing device such as a CT scanning device, a MRI device, an X-ray device, a PET device, and a SPECT device. This implementation is capable of being implemented across a plurality of different computing platforms. Although not shown, this implementation can connect to a network by leveraging connectivity hardware/software such as switches, communications cards, communications libraries, etc. In addition, as described in the above incorporated applications, the raw medical image data being received from the set of modalities 14 via a set of medical image grabbers.

Figure 8:
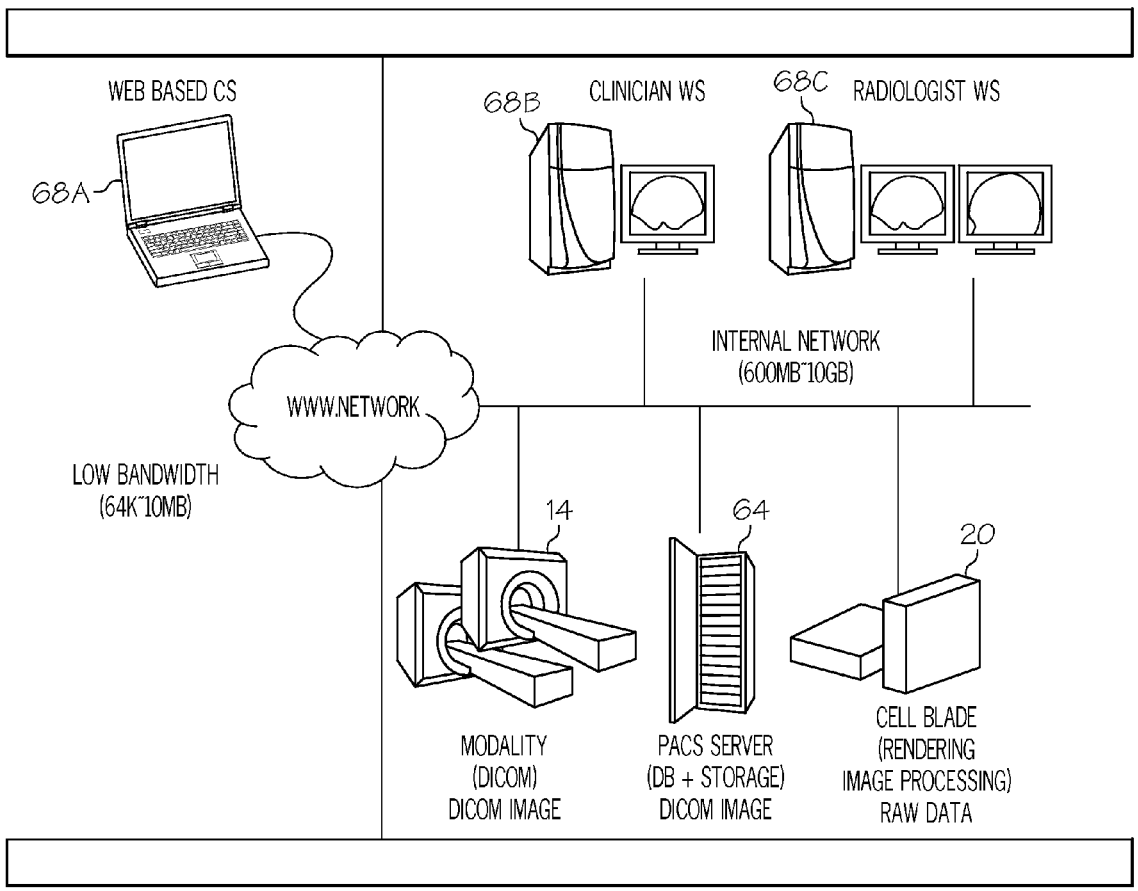
FIG. 8 shows a diagram of a stand-alone hybrid medical image processing system according to the present invention.

Referring now to FIG. 8, a stand-alone hybrid medical image processing system 62 with a Cell BE image processor according to the present invention is shown. Specifically, FIG. 8 depicts thick and thin functional units as typical medical image hosting systems, and the sequencing of the image processing operation of the present invention. Via a switch, this configuration can be connected to the Web. In any event, the medical image is captured through the modality 14 and stored via a set of (e.g., PAC) servers 64. The stored medical image is processed by the (e.g., Cell Blade) processing system 20 for the medical professional(s), and the processed image is shown in the terminal/functional unit 68B-C. The image can also be viewed through the network (e.g. internet) remotely in functional unit 68A. This hybrid medical image processing system can also be tied to a greater healthcare system.

Figure 9:
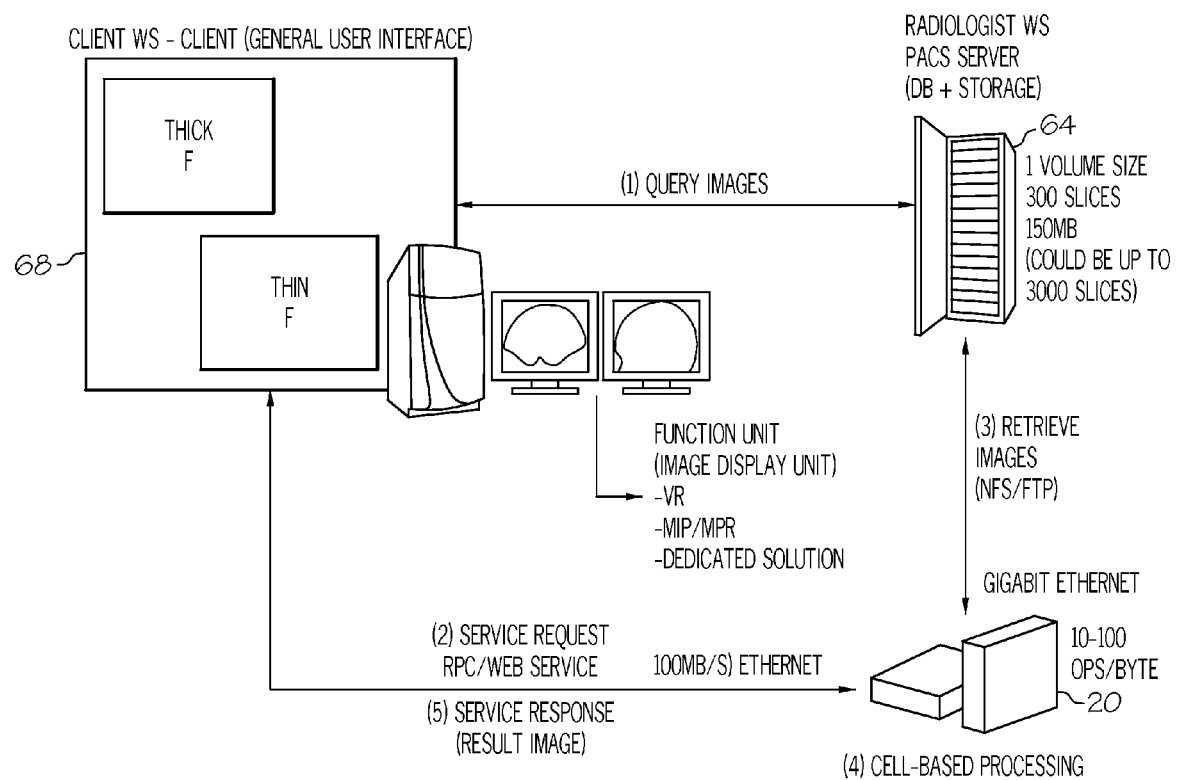
FIG. 9 shows a hybrid medical image processing system implemented over a network according to the present invention.

Referring now to FIG. 9, method steps for the hybrid processing of the present invention will be described. In step 1, the images/image data will be queried from the functional units 68 to the set of servers 64. In step 2, a service request will be issued between functional units 68 and processing system 20. In step 3, the images/image data will be retrieved to processing system 20 from set of servers 64. In step 4, the image data is processed as described above in conjunction with FIG. 7 (e.g., by a pre-processor, a medical image processor, and a post-processor). Once processing is complete, the results (e.g., resulting image and/or associated data) are communicated to and rendered on functional units 68 in step 5.

Figure 10:
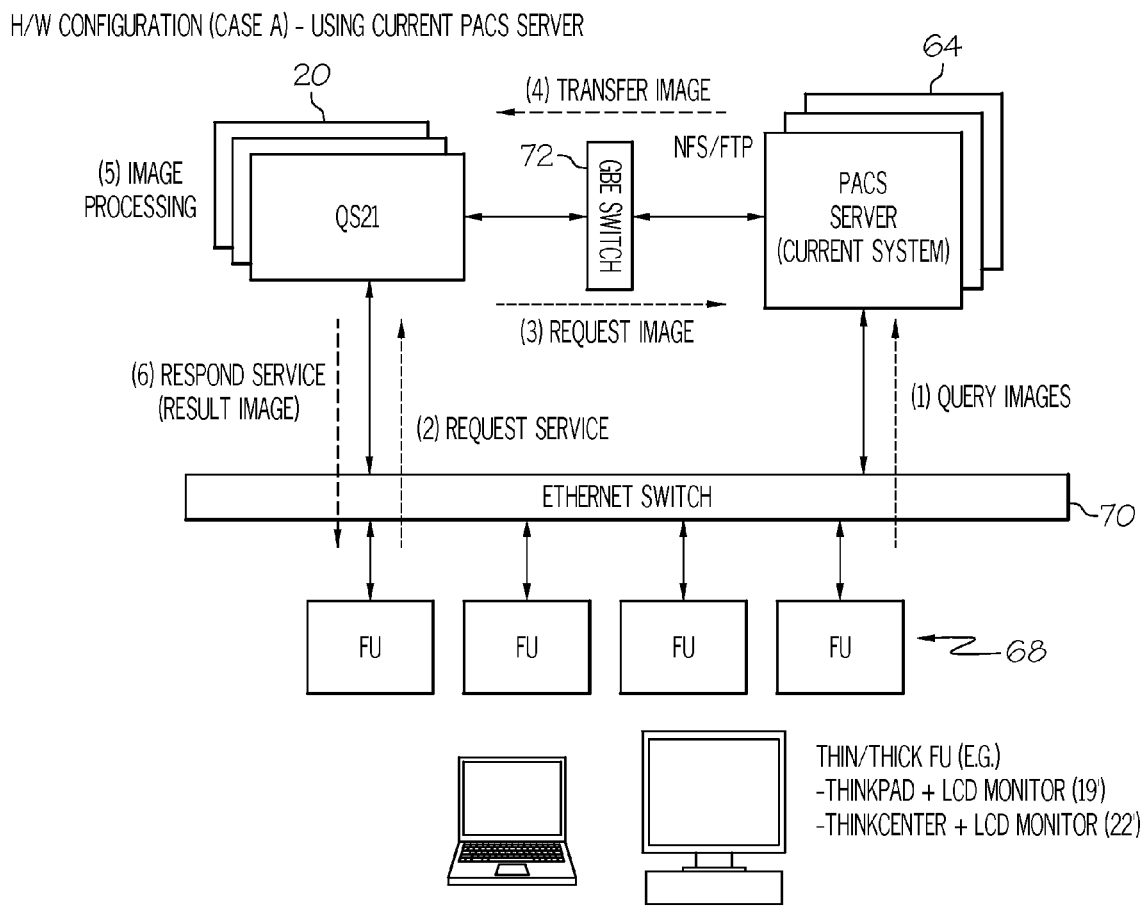
FIG. 10 shows a hardware implementation according to the present invention.

Referring now to FIG. 10, one possible hardware configuration according to then present invention will be shown and described. As depicted, this configuration includes processing system 20 (QS21 processors are shown for illustrative purposes only), set of servers 64 (PACS is shown for illustrative purposes only), and functional units 68. Communication with functional units occurs via Ethernet switch 70, which communication between processing system 20 and set of servers 64 occurs via GbE switch 72. In any event (similar to FIG. 9), in step 1 the images/image data will be queried from the functional units 68 to the set of servers 52. In step 2, a service request will be issued between functional units 68 and processing system 20. In step 3, the images/image data will be requested from set of servers 64. In step 4, the images/image data will be transferred to processing system 20 from set of servers 64. In step 5, the image data is processed as described above in conjunction with FIG. 7 (e.g., by a pre-processor, a medical image processor, and a post-processor). Once processing is complete, the results (e.g., resulting image and/or associated data) are communicated to and rendered on functional units 68 in step 6.

Figure 11:
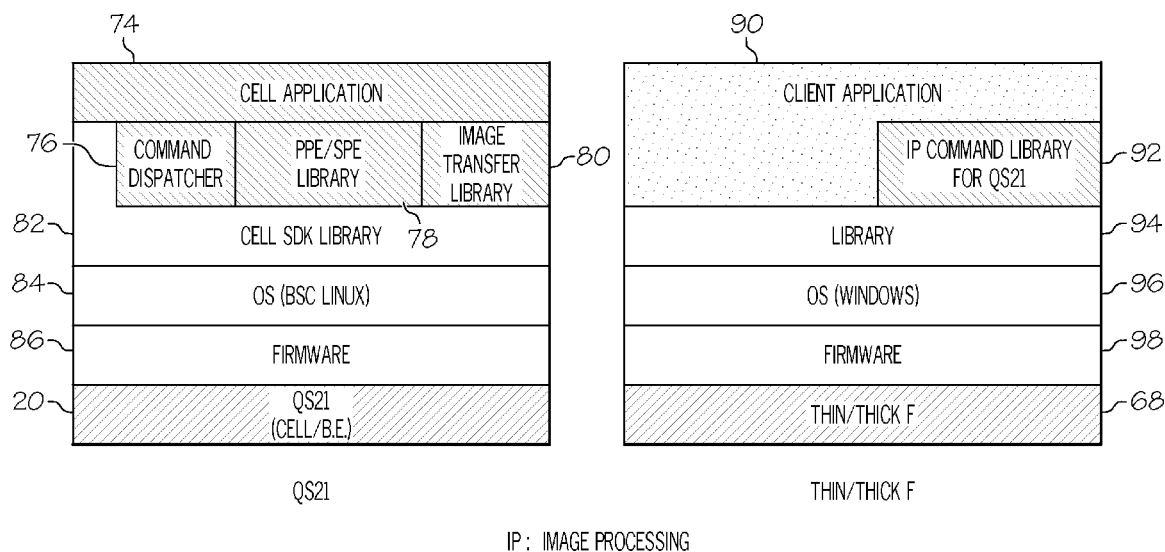
FIG. 11 shows a software stack view based on the hardware implementation of FIG. 10 according to the present invention.

Referring to FIG. 11, software stack diagrams of processing system 20 and functional units 68 are shown in greater detail. As shown, processing system 20 includes the following components having the following functions:

Cell Application 74: Cell Application 74 typically runs on Cell Processor (PPE and SPEs) and receives commands from functional units 68 functional units 68; sends commands to set of servers 64; receives data from set of servers; schedules processing engine tasks according to the commands; processes/calculates the data according to the commands; and sends the result to functional units 68 according to the commands.

Command Dispatcher 76: Command dispatcher 76's function is to recognize commands sent from functional units 68 and distribute the tasks into SPEs or PPE itself.

PPE/SPE Library 78: PPE/SPE Library 78 means Image processing library executed on PPE/SPE (PPE, SPE separately or using both PPE and SPE). The above each task is executed by this library.

Image Transfer Library 80: Image Transfer Library 80 means the functions for transferring images/image data to the functional units 68.

Cell SDK Library 82: Cell SDK Library 82 means built-in functions prepared for Cell/B.E. (SPE Runtime library, SIMD mass library, etc).

Operating System 84: FedoraCore6+Cell patch (Cell patch is included in Cell SDK 2.1).

Firmware 86: Low-level firmware and slim line open firmware developed for QSXX in general.

As further shown, functional units 68 includes the following components having the following functions:

Client Application 90: Clients can develop the inspection application using IP Command Library 92.

IP Command Library 92: IP Command Library 92 means "Image Processing Command Library" and is used as function call by Client Application 90.

Library 94: Library 94 Library means standard library included in SDK of Linux application.

Operating System 96: Windows XP.

Firmware 98: BIOS for x-server in general.

Figure 12:
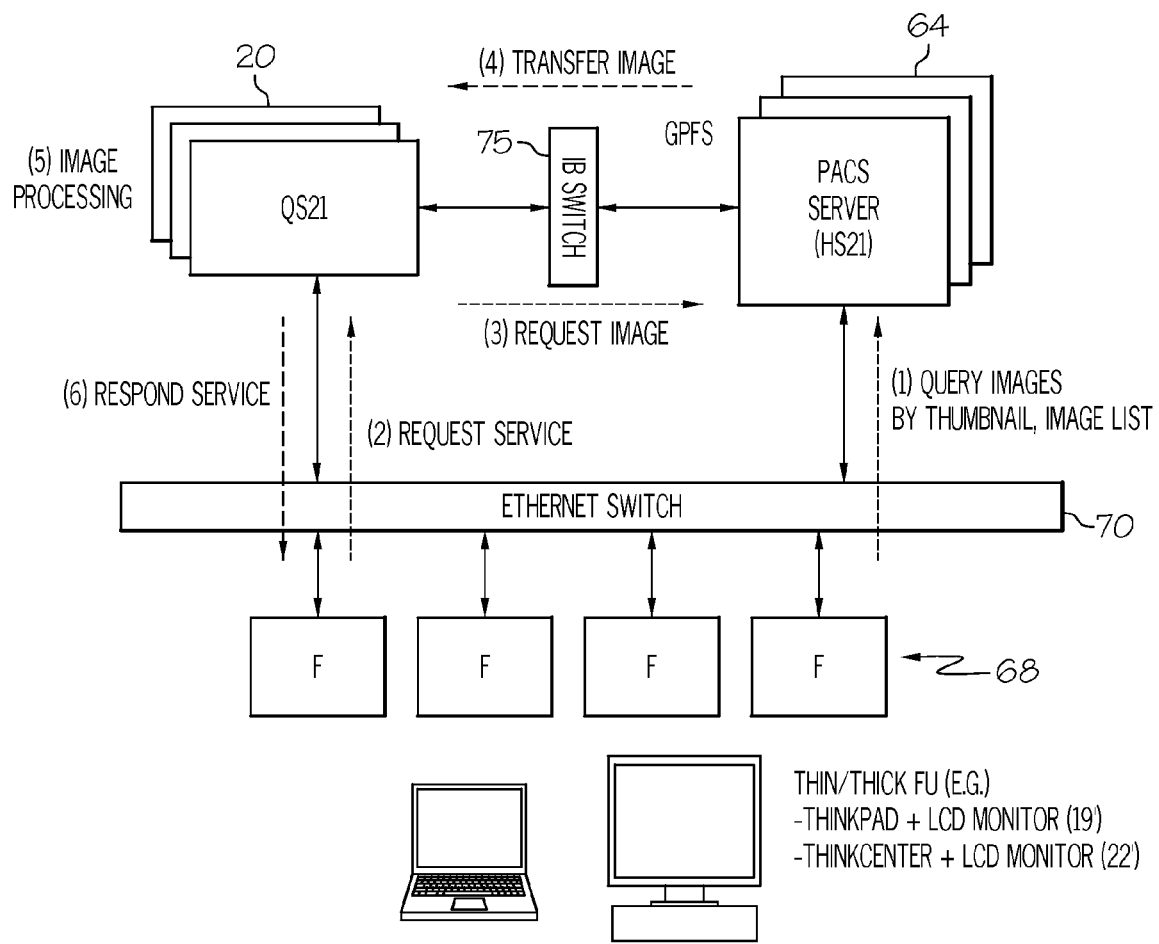
FIG. 12 shows another hardware implementation according to the present invention.

Referring now to FIG. 12, another possible hardware configuration according to then present invention will be shown and described. As depicted, this configuration includes processing system 20, set of servers 64, and functional units 68. Communication with functional units occurs via Ethernet switch 70, which communication between processing system 20 and set of servers 64 occurs via Infiniband switch 75. In any event (similar to FIGS. 9-10), in step 1 the images/image data will be queried from the functional units 68 to the set of servers 52 based on thumbnails and image lists. In step 2, a service request will be issued between functional units 68 and processing system 20. In step 3, the images/image data will be requested from set of servers 64. In step 4, the images/image data will be transferred to processing system 20 from set of servers 64 using InfiniBand communication. In step 5, the image data is processed as described above in conjunction with FIG. 7 (e.g., by a pre-processor, a medical image processor, and a post-processor). Once processing is complete, the results (e.g., resulting image and/or associated data) are communicated to and rendered on functional units 68 in step 6.

Figure 13:
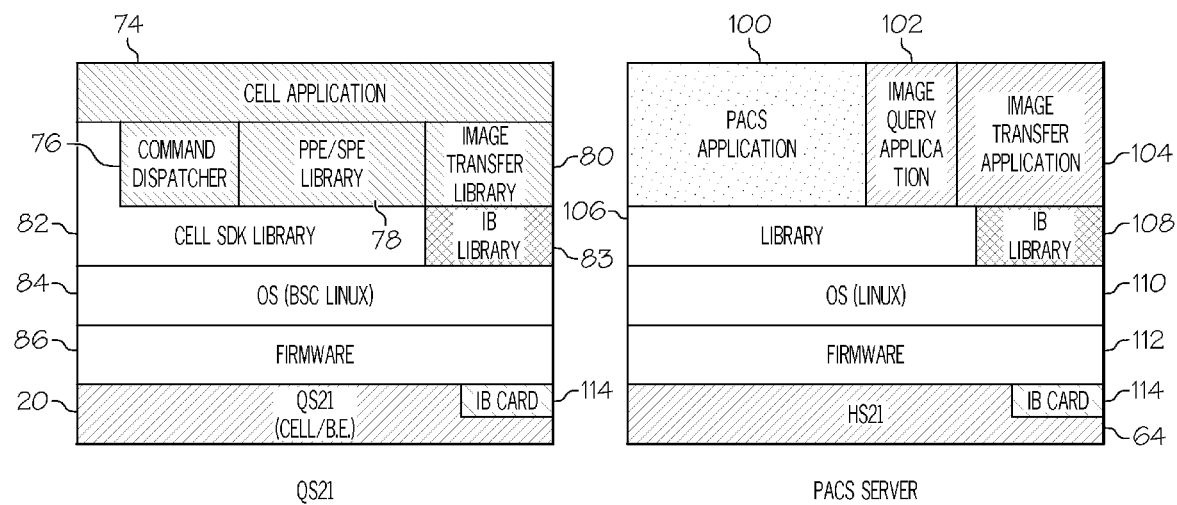
FIG. 13 shows a software stack view based on the hardware implementation of FIG. 12 according to the present invention.

Referring to FIG. 13, software stack diagrams of processing system 20 and functional units 68 are shown in greater detail. As shown, processing system 20 includes the following components having the following functions:

Cell Application 74: Cell Application 74 typically runs on Cell Processor (PPE and SPEs) and receives commands from functional units 68 functional units 68; sends commands to set of servers 64; receives data from set of servers; schedules processing engine tasks according to the commands; processes/calculates the data according to the commands; and sends the result to functional units 68 according to the commands.

Command Dispatcher 76: Command dispatcher 76's function is to recognize commands sent from functional units 68 and distribute the tasks into SPEs or PPE itself.

PPE/SPE Library 78: PPE/SPE Library 78 means Image processing library executed on PPE/SPE (PPE, SPE separately or using both PPE and SPE). The above each task is executed by this library.

Image Transfer Library 80: Image Transfer Library 80 means the functions for transferring images/image data to the functional units 68.

Cell SDK Library 82: Cell SDK Library 82 means built-in functions prepared for Cell/B.E. (SPE Runtime library, SIMD mass library, etc).

IB Library 83: Data/Command transfer library for using InfiniBand such as message passing interface.

Operating System 84: FedoraCore6+Cell patch ( Cell patch is included in Cell SDK 2.1.)

Firmware 86: Low-level firmware and slim line open firmware developed for QSXX in general.

As further shown, each of set of servers 64 includes the following components having the following functions:

Server (e.g. PACS) Application 100: Server Application 100 contains a database that keeps track of every image in the server. It is also a file server to hold the received images.

Image Query Application 102: Image Query Application 102 provides the thumbnail and image list of all files included in the server database for functional units 68.

Image Transfer Application 104: Image Transfer Application 104 sends the image data to functional units 68 according to the functional units' 68 commands.

Library 106: Library 106 Library means standard library included in SDK of Linux application.

IB Library 108: Data/Command transfer library for using InfiniBand such as message passing interface.

Operating System 110: Linux.

Firmware 112: BIOS of HS21.

As further shown, both processing system 20 and set of servers 68 include communications cards such as IB cards 114 for IB communication.

Figure 14:
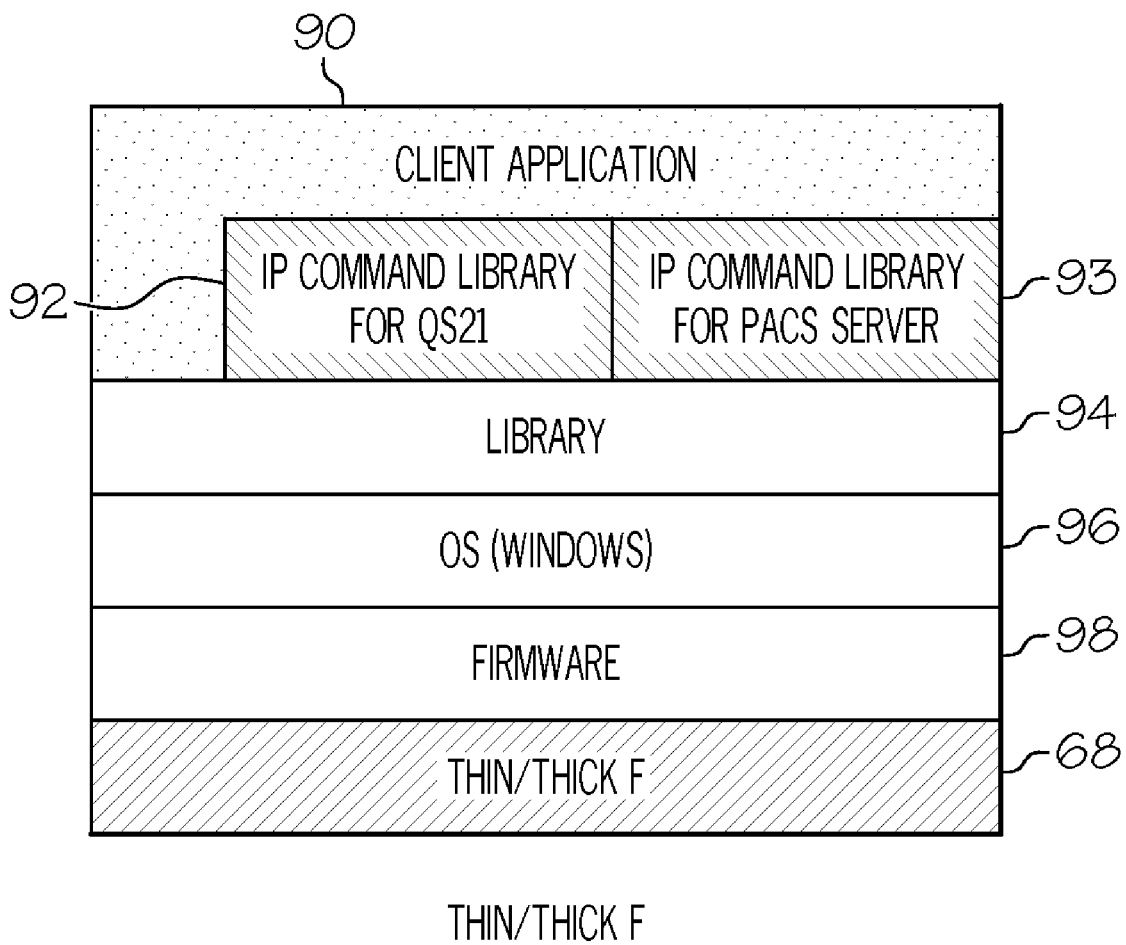
FIG. 14 shows another software stack view based on the hardware implementation of FIG. 12 according to the present invention.

Referring now to FIG. 14, a software stack diagram for functional units 68 based on the implementation of FIG. 12 is shown. As depicted, functional units 68 include the following components having the following functions:

Client Application 90: Clients can develop the inspection application using IP Command Library 92.

IP Command Library 92: IP Command Library 92 means "Image Processing Command Library" and is used as function call by Client Application 90.

IQ Command Library 93: IQ Command Library 93 means "Image Querying Command Library" for PACS Server and is used as function call by Client Application 90.

Library 94: Library 94 Library means standard library included in SDK of Linux application.

Operating System 96: Windows XP.

Firmware 98: BIOS for x-server in general.

II. Computerized Implementation

Figure 15:
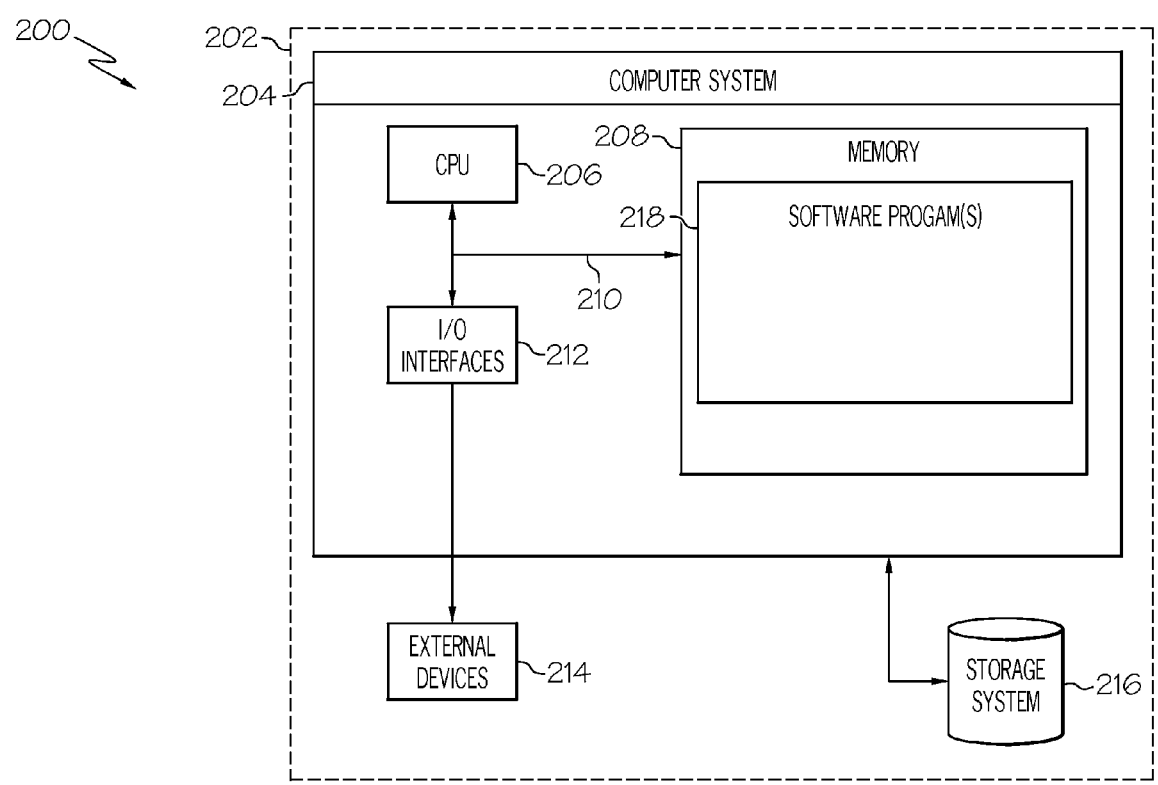
FIG. 15 depicts a more specific computerized implementation according to the present invention.

Referring now to FIG. 15, a more detailed diagram of a computerized implementation 200 of the present invention is shown. As depicted, implementation 200 includes computer system 204 deployed within a computer infrastructure 202. This is intended to demonstrate, among other things, that the present invention could be implemented within a network environment (e.g., the Internet, a wide area network (WAN), a local area network (LAN), a virtual private network (VPN), etc.), or on a stand-alone computer system. In the case of the former, communication throughout the network can occur via any combination of various types of communications links. For example, the communication links can comprise addressable connections that may utilize any combination of wired and/or wireless transmission methods. Where communications occur via the Internet, connectivity could be provided by conventional TCP/IP sockets-based protocol, and an Internet service provider could be used to establish connectivity to the Internet. Still yet, computer infrastructure 202 is intended to demonstrate that some or all of the components of implementation 200 could be deployed, managed, serviced, etc. by a service provider who offers to implement, deploy, and/or perform the functions of the present invention for others.

As shown, computer system 204 includes a processing unit 206, a memory 208, a bus 120, and input/output (I/O) interfaces 212. Further, computer system 204 is shown in communication with external I/O devices/resources 214 and storage system 216. In general, processing unit 206 executes computer program code, such as software program(s) 218, which is stored in memory 208 and/or storage system 206. While executing computer program code, processing unit 206 can read and/or write data to/from memory 18, storage system 206, and/or I/O interfaces 212. Bus 120 provides a communication link between each of the components in computer system 204. External devices 214 can comprise any devices (e.g., keyboard, pointing device, display, etc.) that enable a user to interact with computer system 204 and/or any devices (e.g., network card, modem, etc.) that enable computer system 204 to communicate with one or more other computing devices.

Computer infrastructure 202 is only illustrative of various types of computer infrastructures for implementing the invention. For example, in one embodiment, computer infrastructure 202 comprises two or more computing devices (e.g., a server cluster) that communicate over a network to perform the process(es) of the invention. Moreover, computer system 204 is only representative of various possible computer systems that can include numerous combinations of hardware. To this extent, in other embodiments, computer system 14 can comprise any specific purpose computing article of manufacture comprising hardware and/or computer program code for performing specific functions, any computing article of manufacture that comprises a combination of specific purpose and general purpose hardware/software, or the like. In each case, the program code and hardware can be created using standard programming and engineering techniques, respectively. Moreover, processing unit 206 may comprise a single processing unit, or be distributed across one or more processing units in one or more locations, e.g., on a client and server. Similarly, memory 208 and/or storage system 216 can comprise any combination of various types of data storage and/or transmission media that reside at one or more physical locations. Further, I/O interfaces 212 can comprise any system for exchanging information with one or more external device 214. Still further, it is understood that one or more additional components (e.g., system software, math co-processing unit, etc.) not shown in FIG. 15 can be included in computer system 204. However, if computer system 204 comprises a handheld device or the like, it is understood that one or more external devices 214 (e.g., a display) and/or storage system 216 could be contained within computer system 204, not externally as shown.

Storage system 216 can be any type of system(s) (e.g., databases) capable of providing storage for information under the present invention. To this extent, storage system 216 could include one or more storage devices, such as a magnetic disk drive or an optical disk drive. In another embodiment, storage system 216 include data distributed across, for example, a local area network (LAN), wide area network (WAN) or a storage area network (SAN) (not shown). In addition, although not shown, additional components, such as cache memory, communication systems, system software, etc., may be incorporated into computer system 204.

Shown in memory 208 of computer system 204 is software program(s) 218, which facilitates the functions as described herein. Specifically, software program(s) 218 should be understood to contain one or more of the software components/modules depicted herein.

While shown and described herein as a method and system for processing an image, it is understood that the invention further provides various alternative embodiments. For example, in one embodiment, the invention provides a computer-readable/useable medium that includes computer program code to enable a computer infrastructure to process an image. To this extent, the computer-readable/useable medium includes program code that implements the process(es) of the invention. It is understood that the terms computer-readable medium or computer useable medium comprises one or more of any type of physical embodiment of the program code. In particular, the computer-readable/useable medium can comprise program code embodied on one or more portable storage articles of manufacture (e.g., a compact disc, a magnetic disk, a tape, etc.), on one or more data storage portions of a computing device, such as memory 208 (FIG. 15) and/or storage system 216 (FIG. 15) (e.g., a fixed disk, a read-only memory, a random access memory, a cache memory, etc.), and/or as a data signal (e.g., a propagated signal) traveling over a network (e.g., during a wired/wireless electronic distribution of the program code).

In another embodiment, the invention provides a business method that performs the process of the invention on a subscription, advertising, and/or fee basis. That is, a service provider, such as a Solution Integrator, could offer to transition an organization to an IT service management-oriented organization. In this case, the service provider can create, maintain, support, etc., a computer infrastructure, such as computer infrastructure 202 (FIG. 15) that performs the process of the invention for one or more customers. In return, the service provider can receive payment from the customer(s) under a subscription and/or fee agreement and/or the service provider can receive payment from the sale of advertising content to one or more third parties.

In still another embodiment, the invention provides a computer-implemented method for processing an image. In this case, a computer infrastructure, such as computer infrastructure 202 (FIG. 15), can be provided and one or more systems for performing the process of the invention can be obtained (e.g., created, purchased, used, modified, etc.) and deployed to the computer infrastructure. To this extent, the deployment of a system can comprise one or more of: (1) installing program code on a computing device, such as computer system 204 (FIG. 15, from a computer-readable medium; (2) adding one or more computing devices to the computer infrastructure; and (3) incorporating and/or modifying one or more existing systems of the computer infrastructure to enable the computer infrastructure to perform the process of the invention.

As used herein, it is understood that the terms "program code" and "computer program code" are synonymous and mean any expression, in any language, code or notation, of a set of instructions intended to cause a computing device having an information processing capability to perform a particular function either directly or after either or both of the following: (a) conversion to another language, code or notation; and/or (b) reproduction in a different material form. To this extent, program code can be embodied as one or more of: an application/software program, component software/a library of functions, an operating system, a basic I/O system/driver for a particular computing and/or I/O device, and the like.

A data processing system suitable for storing and/or executing program code can be provided hereunder and can include at least one processor communicatively coupled, directly or indirectly, to memory element(s) through a system bus. The memory elements can include, but are not limited to, local memory employed during actual execution of the program code, bulk storage, and cache memories that provide temporary storage of at least some program code in order to reduce the number of times code must be retrieved from bulk storage during execution. Input/output or I/O devices (including, but not limited to, keyboards, displays, pointing devices, etc.) can be coupled to the system either directly or through intervening I/O controllers.

Network adapters also may be coupled to the system to enable the data processing system to become coupled to other data processing systems, remote printers, storage devices, and/or the like, through any combination of intervening private or public networks. Illustrative network adapters include, but are not limited to, modems, cable modems and Ethernet cards.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

We claim:

1. A hybrid medical image processing system, comprising: a set of servers for receiving medical image data that has not been substantively processed into a medical image from a plurality of medical imaging devices and storing the medical image data in a server database, at least one medical imaging device of the plurality of medical imaging devices being of a different type from at least one other medical imaging device of the plurality of medical imaging devices, the set of servers comprising a server application, a medical image query application, and a medical image transfer application; and
a set of processing systems for processing the stored medical image data into the medical image, the set of processing systems comprising a cell application, a command dispatcher, a processing engine library, and a medical image transfer library.

2. The hybrid medical image processing system of claim 1, further comprising a set of functional units for viewing the medical image data comprising a client application and a medical image processing command library for the set of processing systems.

3. The hybrid medical image processing system of claim 1, the server application being configured to track the medical image data in the server database, and to hold the medical image data in a file server.

4. The hybrid medical image processing system of claim 1, the medical image query application being configured to provide thumbnail and medical image lists of files stored in the server database.

5. The hybrid medical image processing system of claim 1, the medical image transfer application being configured to send the medical image data to a set of functional units based on a command issued by the set of functional units.

6. The hybrid medical image processing system of claim 1, the cell application running on a set of processing engines, and being configured to:
- receive functional commands from a set of functional units;
- send at least a subset of the commands to the set of servers;
- receive the medical image data from the set of servers;
- assign tasks to the set of processing engines to process the medical image data based on the commands; and
- send results from the set of processing engines to the set functional units.

7. The hybrid medical image processing system of claim 1, the set of servers and the set of processing systems each including a communications library, a communications card, an operating system, and firmware.

8. A hybrid medical image processing method, comprising:
- receiving commands from a set of functional units on a set of processing systems;
- sending at least a subset of the commands to a set of servers;
- receiving medical image data from the set of servers, the medical image data having been received from at least one medical imaging device and having not been substantively processed into a medical image;
- assigning tasks for processing the medical image data to a set of processing engines;
- processing the medical image data into the medical image with the set of processing engines; and
- sending results of the processing to the set of functional units.

9. The hybrid medical image processing method of claim 8, further comprising generating the commands on the set of functional units using a client application and a medical image processing command library.

10. The hybrid medical image processing method of claim 8, further comprising interpreting the commands on the set of processing systems using a cell application and a command dispatcher.

11. The hybrid medical image processing method of claim 8, further comprising rendering the medical image data on the set of functional units.

12. A program product stored on at least one computer readable storage medium for processing medical images, the at least one computer readable medium comprising program code for causing at least one computer system to:
- receive commands from a set of functional units on a set of processing systems;
- send at least a subset of the commands to a set of servers;
- receive medical image data from the set of servers, the medical image data having been received from at least one medical imaging device and having not been substantively processed into a medical image;
- assign tasks for processing the medical image data to a set of processing engines;
- process the medical image data into the medical image with the set of processing engines; and
- send results of the processing to the set of functional units.

13. The program product of claim 12, the at least one computer readable medium further comprising program code for causing at least one computer system to generate the commands on the set of functional units using a client application and a medical image processing command library.

14. The program product of claim 12, the at least one computer readable medium further comprising program code for causing at least one computer system to interpret the commands on the set of processing systems using a cell application and a command dispatcher.

15. The program product of claim 12, the at least one computer readable medium further comprising program code for causing at least one computer system to render the medical image data on the set of functional units.

16. A method for deploying a hybrid medical image processing system, comprising:
- deploying a computer infrastructure having at least one computer device being operable to:
- receive commands from a set of functional units on a set of processing systems;
- send at least a subset of the commands to a set of servers;
- receive medical image data from the set of servers, the medical image data having been received from at least one imaging medical device and having not been substantively processed into a medical image;
- assign tasks for processing the medical image data to a set of processing engines;
- process the medical image data into the medical image with the set of processing engines; and
- send results of the processing to the set of functional units.

* * * * *